United States Patent [19]

Wright

[11] 4,243,801

[45] Jan. 6, 1981

[54] 6''-AMINO DERIVATIVES OF 4-0-AMINOGLYCOSYL-6-0-GAROSAMINYL-1,3-DIAMINOCYCLITOLS

[75] Inventor: John J. Wright, Cedar Grove, N.J.

[73] Assignee: Schering Corporation, Kenilworth, N.J.

[21] Appl. No.: 57,136

[22] Filed: Jul. 12, 1979

[51] Int. Cl.³ .................. A61K 31/71; C07H 15/22
[52] U.S. Cl. ........................ 536/17 R; 424/180; 536/10
[58] Field of Search .................... 536/17 R

[56] References Cited

U.S. PATENT DOCUMENTS

| | | | |
|---|---|---|---|
| 3,832,286 | 8/1974 | Weinstein et al. | 536/17 |
| 4,062,947 | 12/1977 | Wright et al. | 536/17 |
| 4,085,208 | 4/1978 | Mallams et al. | 536/17 |

*Primary Examiner*—Johnnie R. Brown
*Attorney, Agent, or Firm*—Elizabeth A. Bellamy; Mary S. King

[57] ABSTRACT

Novel 6''-amino derivatives of 4-0-aminoglycosyl-6-0-garosaminyl-1,3-diaminocyclitols, useful as antibacterial agents, are described.

11 Claims, No Drawings

6''-AMINO DERIVATIVES OF 4-O-AMINOGLYCOSYL-6-O-GAROSAMINYL-1,3-DIAMINOCYCLITOLS

FIELD OF THE INVENTION

This invention relates to novel compositions of matter useful as antibacterial agents. Specifically, this invention relates to 6''-amino derivatives of 4-O-aminoglycosyl-6-O-garosaminyl-1,3-diaminocyclitols useful as antibacterial agents. Further, this invention relates to the 1-N-X, 6'-N-Y derivatives and 5-epi analogs of the foregoing.

Particularly, this invention relates to novel 6''-amino derivatives of 4-O-aminoglycosyl-6-O-garosaminyl-1,3-diaminocyclitol antibacterial agents selected from the group consisting of gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-52, L Antibiotic G-418, Antibiotic JI-20A, Antibiotic JI-20B, Antibiotic Mu-1, antibiotic Mu-2, Antibiotic Mu-4, Antibiotic Mu-5, and Antibiotic Mu-6.

COMPOSITION OF MATTER ASPECT

This invention relates to novel aminoglycoside antibiotics containing a garosamine moiety in which the 6''-methyl group is functionalized by an amino group. Particularly, this invention relates to the 6''-amino derivatives of a 4-O-aminoglycosyl-6-O-garosaminyl-1,3-diaminocyclitol antibacterial agent and the pharmaceutically acceptable acid addition salts thereof. More specifically, the 6''-amino derivatives of a 4-O-aminoglycosyl-6-O-garosaminyl-1,3-diaminocyclitol selected from the group consisting of gentamicin B, gentamicin $B_1$, gentamicin $C_1$, gentamicin $C_{1a}$, gentamicin $C_2$, getamicin $C_{2a}$, gentamicin $C_{2b}$, gentamicin $X_2$, sisomicin, verdamicin, Antibiotic G-52, Antibiotic G-418, Antibiotic JI-20A, Antibiotic JI-20B, Antibiotic Mu-1, Antibiotic Mu-2, Antibiotic Mu-4, Antibiotic Mu-5, and Antibiotic Mu-6.

Further, this invention relates to the 1-N-X derivatives of the foregoing wherein X is a substituent selected from the group consisting of alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl and tolyl, said substituent having up to 8 carbon atoms and, when substituted by both amino and hydroxy groups, said groups are on different carbon atoms.

Still further, this invention relates to the 5-epi analogs of the 6''-amino compounds wherein the 4-O-aminoglycosyl-6-O-garosaminyl-1,3-diaminocyclitol is selected from the group consisting of gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, verdamicin, Antibiotic G-52, Antibiotic G-418, Antibiotic JI-20A, Antibiotic JI-20B, Antibiotic Mu-1 and Antibiotic Mu-4.

Additionally, contemplated within the scope of this invention are the 6'-N-Y derivatives of the 6''-amino derivatized compounds wherein the 4-O-aminoglycosyl-6-O-garosaminyl-1,3-diaminocyclitol is selected from the group consisting of gentamicin B, gentamicin $C_{1a}$, sisomicin, Antibiotic JI-20A, Antibiotic Mu-1, Antibiotic Mu-2, Antibiotic Mu-4, Antibiotic Mu-5 and Antibiotic Mu-6, wherein Y is a substituent selected from the group consisting of alkyl, alkenyl, cycloalkyl, cycloalkylalkyl, hydroxyalkyl, aminoalkyl, alkylaminoalkyl, aminohydroxyalkyl, alkylaminohydroxyalkyl, said Y having from 2 to 8 carbon atoms, and when substituted by both amino and hydroxy groups, said groups are on different carbon atoms.

Particularly valuable and preferred compounds of this invention are as follows:
(a) 6''-aminoverdamicin,
(b) 6''-aminosisomicin,
(c) 6''-aminogentamicin $C_1$,
(d) 6''-aminogentamicin $C_2$,
(e) 5-epi-6''-aminosisomicin,
(f) 1-N-ethyl-6''-aminosisomicin.

Also included within the composition-of-matter aspect of this invention are the pharmaceutically acceptable acid addition salts of the 6''-amino derivatives. The salts which are contemplated are made according to known procedures such as by neutralizing the free base with the appropriate acid, usually to about pH 5. Included among the pharmaceutically acceptable acid addition salts of this invention are those derived from organic acids such as succinic, fumaric and maleic, or preferably from inorganic acids such as hydrochloric, sulfuric, phosphoric, and hydrobromic. The physical embodiments of the acid addition salts of this invention are characterized by being white solids which are soluble in water, sparingly soluble in most polar organic solvents, and insoluble in most non-polar organic solvents.

PROCESS ASPECT OF THE INVENTION

The 4-O-aminoglycosyl-6-O-garosaminyl-1,3-diaminocyclitol starting compounds of my invention, for example, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-52, Antibiotic G-418, Antibiotic JI-20A, Antibiotic JI-20B, Antibiotic Mu-1, Antibiotic Mu-2, Antibiotic Mu-4, Antibiotic Mu-5 and Antibiotic Mu-6 are known antibiotics. Methods for the preparation of their 1-N-X derivatives, 5-epi analogs, and 6'-N-Y derivatives are described in U.S. Pat. Nos. 4,002,742, 4,000,261 and 4,044,123, respectively.

I have found it advantageous to prepare the 6''-amino derivatives of my invention after 1-N-X, or 5-epi-, or 6'-N-Y derivatizaton has been accomplished.

The novel 6''-amino-4-O-aminoglycosyl-6-O-garosaminyl-1,3-diaminocyclitols of my invention as described hereinabove are prepared by elaboration of techniques as described hereinbelow.

The starting aminoglycoside is per-N-protected via techniques well known in the art. In this application, "per-N-protected" refers to protection of all amino groups on the molecule. The amino protecting group I preferably utilize is benzyloxycarbonyl, however, other arylalkyloxycarbonyl blocking groups can be used, such as p-methoxybenzyloxycarbonyl. Still other blocking groups selected from the alkyloxycarbonyl class can be used, e.g., ethoxycarbonyl, t-butoxycarbonyl and 2,2,2-trichloroethoxycarbonyl. The per-N-blocked aminoglycoside is then treated with acetic anhydride in pyridine to block all hydroxyl groups other than the spacially hindered 4''-OH group with an acetate blocking group. It is understood that in those instances where the 1-N or 6'-N positions have been derivatized with moieties containing amino and/or hydroxyl groups that these groups will also be blocked. For ease of explanation poly-protection, in this case poly-OH protection, refers to protection at specific OH sites, those not mentioned being unprotected.

The per-N-protected-poly-OH-protected aminoglycoside is then treated with p-toluenesulfonylisocyanate to form the 4''-O-tosylurethane. This compound is then N-methylated with methyl iodide and potassium carbonate to form the 4''-O-(N-methyl)tosylurethane which is then treated with hydrazine to prepare the 4''-O-hydrazide and deblock the hydroxyl groups. The 4''-O-hydrazide is then oxidized with nitrous acid to prepare the azidoformate and then heated to produce the 4''-O,6''-C-oxazolidinone. The oxazolidinone is then deblocked in a manner dependent on the substrate. The deblocking may be by hydrogenation or the use of sodium in liquid ammonia. The latter method is applicable where the substrate has 4'(5') unsaturation. The unblocked oxazolidinone is then treated with strong base to obtain the desired 6''-amino aminoglycoside.

METHOD-OF-USE AND PHARMACEUTICAL COMPOSITION ASPECT

In general, the compounds of my invention and their pharmaceutically acceptable acid addition salts exhibit activity against a broad range of gram-negative pathogens and have a spectrum and potency similar to or greater than their parent compounds but with reduced toxicity. The pathogenic types of bacteria against which our compounds exhibit activity are the gram-negatives such as *E. coli*, Klebsiella, Proteus, Providencia, Pseudomonas, Salmonella, and Serratia, and the gram-positives such as Staphylococcus and *B. subtilis*.

The compounds of my invention can be used alone or in combination with other antibiotic agents to prevent the growth or reduce the number of bacteria in various environments. Their activity against gram-negative bacteria renders them useful in combating infection in human or veterinary application. Additionally, our compounds may also be used to disinfect laboratory glassware, dental and medical equipment.

In general, the dosage administered of my compound will be dependent on the age and weight of the animal species being treated, mode of administration and the type and severity of bacterial infection being prevented or reduced.

The compounds of my invention may be administered orally, compounded in the form of tablets, capsules, elixirs or the like, or administered with animal feed. It is in these dosage forms that these antibacterials are most effective for treating bacterial infections of the gastrointestinal tract, which infection cause diarrhea. They are also useful in pre- and post-operative gut sterilization.

In liquid form they may be administered parenterally via intramuscular, intravenous, subcutaneous and intrasternal injection. The injectable solution or suspension will usually be administered at from about 1 mg. to about 30 mgs. of antibacterial per kilogram of body weight per day divided into about 2 to about 4 doses. The precise dose will depend on the stage and severity of the infection, the susceptibility of the infecting organism to the antibacterial and the individual characteristics of the animal species being treated. They may also be utilized in liquid form such as solutions, suspensions and the like, for otic and ophthalmic use.

Further, the compounds of this invention may be applied topically in the form of ointments, both hydrophilic and hydrophobic, lotions which may be aqueous, non-aqueous or other emulsion types, or in creams or gels. In general, the topical applications will contain from about 0.1 to about 3.0 gms. of the active per 100 gms. of ointment, cream or lotion. The topical preparations are usually gently applied to lesions from about 2 to about 5 times a day.

The pharmaceutical carriers useful in the preparation of all the foregoing formulations will include, for example, such substances as water, oils, fats, waxes, polyesters, alcohols, polyols and the like.

The invention described hereinabove is illustrated in detail hereinbelow in the Preparations, Examples and Formulations, which is not to be construed as limiting the scope of my invention.

PREPARATIONS

Preparation 1

Poly-O-Protected-Per-N-Protected Aminoglycosides

A.

5,2''-Di-O-Acetyl-1,3,2',6',3''-Penta-N-Benzyloxycarbonylgentamicin $C^2$

A mixture of 1,3,2',6',3''-penta-N-benzyloxycarbonylgentamicin $C_2$ (68.7 g.) in pyridine (550 ml) and acetic anhydride (250 ml) is heated at 60° for 24 hours. The solution is evaporated under high vacuum to leave a residue which is taken up in chloroform. The organic layer is washed with water (2×200) and dried over magnesium sulfate. Column chromatography on 0.8 kg of silica gel eluting with 2% methanol on chloroform followed by evaporation of the pooled homogeneous eluates produces the title compound: $[\alpha]_D^{26} + 84.8°$ (EtOH).

B. By Substituting the appropriately N-blocked aminoglycoside in Preparation 1A for the N-blocked gentamicin $C_2$, there is obtained the following:

(a) 5,2''-di-O-acetyl-1,3,2',6',3''-penta-N-benzyloxycarbonylsisomicin, (b) 5,2''-di-O-acetyl-1,3,2',6',3''-penta-N-benzyloxycarbonylverdamicin, (c) 5,2''-di-O-acetyl-1,3,2',6',3''-penta-N-benzyloxycarbonylgentamicin $C_1$, (d) 5,2''-di-O-acetyl-1,3,2',6',3''-penta-N-benzyloxycarbonyl-5-epi-sisomicin, (e) 5,2''-di-O-acetyl-1,3,2',6',3''-penta-N-benzyloxycarbonyl-1-N-ethylsisomicin.

Preparation 2

Poly-O-Protected-4''-O-(N-Methyl-N-Tosylcarbamoyl)-Per-N-Protected-Aminoglycosides A. Preparation of 2'',5-Di-O-Acetyl-4''-O-(N-Methyl-N-Tosylcarbamoyl)-1,3,2',6',3''-penta-N-Benzyloxycarbonylgentamicin $C_2$ 2'',5-Di-O-acetyl-1,3,2',6',3''-penta-N-benzyloxycarbonylgentamicin $C_2$ (61.05 g) is dissolved in acetonitrile (600 ml) and p-toluenesulfonyl isocyanate (15 g) is added and the mixture is allowed to stir at room temperature overnight. Water (0.5 ml) is added and stirring continued for 1 hour. The solvents are evaporated in vacuo to give a foamy solid residue (75.4 g). The residue is dissolved in acetone (600 ml) and treated with methyl iodide (40 ml) and potassium carbonate (50 g) at room temperature. The mixture is allowed to stir overnight before being filtered and concentrated under vacuum to give a residue.

Chromatography by high pressure liquid chromatography on silica gel in 0.1% methanol in chloroform followed by evaporation of the pooled homogeneous eluates yields the title compound: $[\alpha]_D^{26} +102.5°$ (EtOH)

B. By substituting the compounds of Preparation 1B(a–e), in Preparation 2A, there is obtained the following:
(a) 5,2″-di-O-acetyl-4″-O-(N-methyl-N-tosylcarbamoyl)-1,3,2′,6′,3″-penta-N-benzyloxycarbonylsisomicin,
(b) 5,2″-di-O-acetyl-4″-O-(N-methyl-N-tosylcarbamoyl)-1,3,2′,6′,3″-penta-N-benzyloxycarbonylverdamicin,
(c) 5,2″-di-O-acetyl-4″-O-(N-methyl-N-tosylcarbamoyl)-1,3,2′,6′,3″-penta-N-benzyloxycarbonyl-gentamicin $C_1$.
(d) 5,2″-di-O-acetyl-4″-O-(N-methyl-N-tosylcarbamoyl)-1,3,2′,6′,3″-penta-N-benzyloxycarbonyl-5-epi-sisomicin,
(e) 5,2″-di-O-acetyl-4″-O-(N-methyl-N-tosylcarbamoyl)-1,3,2′,6′,3″-penta-N-benzyloxycarbonyl-1-N-ethylsisomicin.

Preparation 3

4″-O-Hydrazido-Per-N-Protected Aminoglycosides

A.

4″-O-Hydrazido-1,3,2′,6′,3″-Penta-N-Benzyloxycarbonylgentamicin $C_2$

To a solution of 2″,5-di-O-acetyl-4″-O-(N-methyl-N-tosylcarbamoyl)-1,3,2′,6′,3″-penta-N-benzyloxycarbonyl-gentamicin $C_2$ (14.2 g) in anhydrous ethanol (100 ml) under $N_2$ is added 90% hydrazine (50 ml), and the whole left at room temperature for 3 days. Evaporation of the solvents yields a foamy solid which is chromatographed on silica gel and eluted with 3% methanol/chloroform followed by concentration of the pooled homogeneous eluates to yield the title compound: $[\alpha]_D^{26} +99.3°$ (EtOH).

B. In a manner similar to Preparation 3A, by substituting the products of Preparation 2B(a–e) there is obtained the following:
(a) 4″-O-hydrazido-1,3,2′,6′,3″-penta-N-benzyloxycarbonylsisomicin,
4″-O-hydrazido-1,3,2′,6′,3″-penta-N-benzyloxycarbonylverdamicin,
(c) 4″-O-hydrazido-1,3,2′,6′,3″-penta-N-benzyloxycarbonylgentamicin $C_1$,
(d) 4″-O-hydrazido-1,3,2′,6′,3″-penta-n-benzyloxycarbonyl-5-epi-sisomicin,
(e) 4″-O-hydrazido-1,3,2′,6′,3″-penta-N-benzyloxycarbonyl-1-N-ethylsisomicin.

Preparation 4

4″-O-Azidocarbonyl-Per-N-Protected Aminoglycosides

A.

4″-O-Azidocarbonyl-1,3,2′,6′,3″-Penta-N-Benzyloxycarbonylgentamicin $C_2$

4″-O-Hydrazido-1,3,2′,6′,3″-penta-N-benzyloxycarbonylgentamicin $C_2$ (11.9 g) is dissolved in acetic acid (glacial, 50 ml) and water (6 ml). Sodium nitrite (1.38 g) is added in water (12 ml) at 5° C. After the addition is complete, the reaction is stirred at room temperature for forty minutes. Water is added (500 ml) and the solution extracted with ether, (3×500 ml). The ether extracts are washed with saturated sodium bicarbonate (2×60 ml) and water and dried over $MgSO_4$. The residue obtained on evaporation of the ether is chromatographed on silica gel in 2% methanol in chloroform which, after concentration of the pooled homogeneous eluates followed by precipitation of the residue from ether-hexane (1:3), yields the title compound: $[\alpha]_D^{26} +112°$ (EtOH); $\nu(CHCl_3)$ (cm$^{-1}$) 2150, 1710.

B. In a manner similar to Preparation 4A, by substituting the products of Preparation 3B(a–e) there is obtained the following:
(a) 4″-O-azidocarbonyl-1,3,2′,6′,3″-penta-N-benzyloxycarbonylsisomicin,
(b) 4″-O-azidocarbonyl-1,3,2′,6′,3″-penta-N-benzyloxycarbonylverdamicin,
(c) 4″-O-azidocarbonyl-1,3,2′,6′,3″-penta-N-benzyloxycarbonylgentamicin $C_1$,
(d) 4″-O-azidocarbonyl-1,3,2′,6′,3″-penta-N-benzyloxycarbonyl-5-epi-sisomicin,
(e) 4″-O-azidocarbonyl-1,3,2′,6′,3″-penta-N-benzyloxycarbonyl-1-N-ethylsisomicin.

EXAMPLES

Example 1

6″-Amino Aminoglycosides

A. 6″-Aminogentamicin $C_2$

4″-O-Azidocarbonyl-1,3,2′,6′,3″-penta-N-benzyloxycarbonylgentamicin $C_2$ (5.3 g) is heated in dichloromethane at 130° C. for 18 hours. The solvent is removed in vacuo and the residue chromatographed on silica gel in 2% methanol in chloroform to yield, as the most polar product, 4″,6″-O,N-carbonyl-1,3,2′,6′,3″-penta-N-benzyloxycarbonyl-gentamicin $C_2$. This material is dissolved in 20% aqueous dioxane (35 ml) and treated with 10% palladium-on-carbon (100 mg) and hydrogen (55 psi) for 18 hours. The catalyst is removed by filtration and the solvent removed. The residue is treated with 1 N sodium hydroxide at reflux for 18 hours. The solution is then neutralized by the addition of 1 N sulfuric acid to pH 10, concentrated and dropped into absolute ethanol. The resultant precipitate is filtered and the filtrate is evaporated to dryness and the residue chromatographed on silica gel in a chloroform/methanol/ammonium hydroxide (28%) (1:1:1) solvent mixture to obtain the title compound after passage through IR 401S (OH$^-$) ion-exchange resin: $[\alpha]_D^{26} +136°$ (EtOH); $[\theta] -4100$ (TACu); pmr ($D_2O$) δ1.1 (d, 3H, CH-$\underline{CH_3}$); 3.9 (dd, J=3.5, 14 Hz, 2H, H-2″); 4.15 (d, J=12.5 Hz, 1H, H-5 eq); 5.12 (m, 4H, H-1′ and H-1″). In acid, δ5.15 (d, J=4 Hz, H-1″); δ5.8 (d, J=4 Hz, H-1′); cmr (TMS) ($D_2O$) δ102.4 (C-1′), 101.0 (C-1″), 88.2 (C-4), 87.5 (C-6), 75.3 (C-5), 75.0 (C-4″), 74.0 (C-5′), 70.1 (C-2″), 65.7 (C-5″), 61.3 (C-3″), 51.6 (C-1), 51.2 (C-3), 50.5 (C-6′), 50.1 (C-2′), 45.9 (C-6″), 37.1 (C-7″), 36.5 (C-2), 26.6 (C-3′), 25.8 (C-4′), 18.3 (C-7′).

B. Treat the product of Preparation 4B(c) in the manner of Example 1A to obtain the following:
(a) 6″-aminogentamicin $C_1$.

C. Treat the products of Preparation 4B(a,b,d,e) in the manner of Example 1A, except in view of the 4′(5′)-unsaturation in these compounds, remove the N-blocking groups via liquid ammonia and sodium rather than hydrogenation to obtain the following:
(a) 6″-aminosisomicin
(b) 6″-aminoverdamicin
(c) 6″-amino-5-epi-sisomicin
(d) 6″-amino-1-N-ethylsisomicin.

EXAMPLE 2

Acid Addition Salts

A. Sulfate Salts (Sulfuric Acid Addition Salts)

Dissolve 5 gm. of 6″-aminogentamicin $C_2$ in 25 ml of water and adjust the pH of the solution to 4.5 with 1 N sulfuric acid. Pour into about 300 ml of methanol with vigorous agitation, continue the agitation for about 10–20 minutes and filter. Wash the precipitate with methanol and dry at about 60° C. in vacuo to obtain the corresponding 6″-aminogentamicin $C_2$ sulfate.

B. Hydrochloride Salts

Dissolve 5 gm. of 6″-aminogentamicin $C_2$ in 25 ml. of water. Acidify the 2 N hydrochloric acid to pH 5. Lyophilize to obtain the corresponding 6″-aminogentamicin $C_2$ hydrochloride.

I claim:

1. The 6″-amino derivative of a 4-O-aminoglycosyl-6-O-garosaminyl-1,3-diaminocyclitol antibacterial agent, and the pharmaceutically acceptable acid addition salts thereof.

2. A compound of claim 1 wherein the 4-O-aminoglycosyl-6-O-garosaminyl-1,3-diaminocyclitol is selected from the group consisting of gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, sisomicin, verdamicin, Antibiotic G-52, Antibiotic G-418, Antibiotic JI-20A, Antibiotic JI-20B, Antibiotic Mu-1, Antibiotic Mu-2, Antibiotic Mu-4, Antibiotic Mu-5, and Antibiotic Mu-6.

3. The 1-N-X derivatives of a compound of claim 2 wherein X is a substituent selected from the group consisting of alkyl, alkenyl, cycloalkyl, cycloalkylalkyl, hydroxyalkyl, aminoalkyl, alkylaminoalkyl, aminohydroxyalkyl, alkylaminohydroxyalkyl, phenyl, benzyl and tolyl, said subtituent having up to 8 carbon atoms and, when substituted by both amino and hydroxy groups, said groups are on different carbon atoms.

4. The 5-epi derivatives of a compound of claim 1 wherein the 4-O-aminoglycosyl-6-O-garosaminyl-1,3-diaminocyclitol is selected from the group consisting of gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, verdamicin, Antibiotic G-52, Antibiotic G-418, Antibiotic JI-20A, Antibiotic JI-20B, Antibiotic Mu-1 and Antibiotic Mu-4.

5. The 6′-N-Y- derivatives of a compound of claim 1 wherein the 4-O-aminoglycosyl-6-O-garosaminyl-1,3-diaminocyclitol is selected from the group consisting of gentamicin B, gentamicin $C_{1a}$, sisomicin, Antibiotic JI-20A, Antibiotic Mu-1, Antibiotic Mu-2, Antibiotic Mu-4, Antibiotic Mu-5 and Antibiotic Mu-6, wherein Y is a substituent selected from the group consisting of alkyl, alkenyl, cycloalkyl, cycloalkylalkyl, hydroxyalkyl, aminoalkyl, alkylaminoalkyl, aminohydroxyalkyl, alkylaminohydroxyalkyl, said Y having from 2 to 8 carbon atoms, and when substituted by both amino and hydroxy groups, said groups are on different carbon atoms.

6. A compound of claim 2 which is 6″-aminoverdamicin.

7. A compound of claim 2 which is 6″-aminogentamicin $C_2$.

8. A compound of claim 2 which is 6″-aminogentamicin $C_1$.

9. A compound of claim 2 which is 6″-aminosisomicin.

10. A compound of claim 3 which is 1-N-ethyl-6″-aminosisomicin.

11. A compound of claim 4 which is 5-epi-6″-aminogentamicin $C_2$.

* * * * *